United States Patent [19]

Long

[11] 4,060,456

[45] * Nov. 29, 1977

[54] GLUCOSE ISOMERIZATION PROCESS

[75] Inventor: Margaret E. Long, Winston-Salem, N.C.

[73] Assignee: R. J. Reynolds Tobacco Company, Winston-Salem, N.C.

[ * ] Notice: The portion of the term of this patent subsequent to June 28, 1991, has been disclaimed.

[21] Appl. No.: 621,713

[22] Filed: Oct. 14, 1975

Related U.S. Application Data

[63] Continuation of Ser. No. 320,034, Jan. 2, 1973, abandoned, which is a continuation-in-part of Ser. No. 161,337, July 9, 1971, Pat. No. 3,821,086.

[51] Int. Cl.$^2$ ............................................. C12D 13/00
[52] U.S. Cl. ................................. 195/31 F; 195/65; 195/115; 195/DIG. 11
[58] Field of Search ................. 195/31 F, 63, 68, 115, 195/65, 73; 210/18

[56] References Cited

U.S. PATENT DOCUMENTS

| | | | |
|---|---|---|---|
| 3,356,609 | 12/1967 | Bruemmer | 210/18 |
| 3,594,325 | 7/1971 | Feiersten et al. | 195/68 |
| 3,645,848 | 2/1972 | Lee et al. | 195/31 F |
| 3,694,314 | 9/1972 | Loyd et al. | 195/31 F |
| 3,695,999 | 10/1972 | Forgione et al. | 195/68 |

*Primary Examiner*—Raymond N. Jones
*Assistant Examiner*—Thomas G. Wiseman
*Attorney, Agent, or Firm*—Manford R. Haxton; Herbert J. Bluhm

[57] ABSTRACT

Microbial cell material having a glucose-isomerizing enzyme associated therewith is subjected to flocculation conditions to produce a flocculated aggregate containing the cell material. Glucose syrups are brought into contact with the flocculated aggregates and a portion of the glucose is thereby converted to fructose in the presence of the glucose-isomerizing enzyme.

9 Claims, 2 Drawing Figures

GLUCOSE ISOMERIZATION PROCESS

This is a continuation of application Ser. No. 320,034 filed Jan. 2, 1973, now abandoned, which, in turn, is a continuation-in-part of application Ser. No. 161,337 filed July 9, 1971, now U.S. Pat. No. 3,821,086.

SUMMARY OF THE INVENTION

This invention relates to a process for isomerizing glucose to fructose in the presence of a glucose-isomerizing enzyme derived from a microorganism. More specifically, this invention relates to the use of polymeric flocculants for immobilizing microbial cells or cell debris having glucose-isomerizing enzymes associated therewith. The resulting flocculated material containing the enzyme is particularly suitable for use in a continuous glucose isomerization process.

BACKGROUND OF THE INVENTION

The ready availability of glucose and the superior sweetening power of syrups containing fructose have long made it desirable to find a practical method for converting glucose to fructose. The alkaline isomerization of glucose to fructose has been extensively investigated by many workers but the yields obtained from such a reaction are less than satisfactory due to the formation of significant amounts of unwanted by-products. In recent years, however, an alternative method has received considerable attention which is based on the discovery that certain microorganisms are capable of elaborating an enzyme which isomerizes glucose to fructose. U.S. Pat. Nos. relating to enzymatic glucose isomerization processes include 2,950,228, 3,616,221, 3,622,463, 3,623,953, 3,625,828, 3,645,848, 3,654,080 and 3,689,362.

In spite of the promising aspects offered by the enzymatic approach to glucose isomerization, production costs and efficient utilization of glucose isomerase enzyme preparations present formidable obstacles to the development of a commercially practical glucose isomerization process. Since most of the microorganisms known to produce glucose isomerase involve intracellular isomerase, the present state of technology relating to the production and use of cell-free isomerase preparations makes the adoption of a glucose isomerization process based thereon economically unattractive. Consequently, primary interest has centered on processes which utilize the isomerase-containing microbial cells in such a way that repeated use of the enzyme is achieved.

U.S. Pat. No. 3,694,314 describes one such process in which a Streptomyces organism is cultured under aerobic conditions and the cellular material is treated with filter aid before harvesting same by vacuum filtration using a rotary drum vacuum filter. The filter cake is subsequently dried, then slurried with a glucose-containing solution that is pumped through a pressure leaf filter to give a relatively thin layer of cell-containing material on the leaves of the filter. A glucose solution is then passed through the pressure leaf filter to obtain an effluent syrup containing mixtures of glucose and fructose. Although this process is reasonably effective, the degree of control is less than satisfactory in that cellular material bed depths and glucose solution flow rates must be maintained within certain limits in order to achieve acceptable operation. Equipment and maintenance costs relating to the process apparatus represent further disadvantages.

This invention provides a simple but effective means for immobilizing glucose isomerase so that it may be used repeatedly in either a continuous- or batch-type process. Moreover, the properties of the immobilized isomerase are such that relatively simple apparatus can be used to carry out the glucose isomerization. The physical properties and enzymatic activity of the immobilized isomerase material produce excellent glucose conversion rates at relatively high flow rates of substrate solution.

DESCRIPTION OF THE INVENTION

Briefly, this invention involves the use of a polyelectrolyte as an aggregate-forming support material for microbial cellular material containing isomerase. The enzyme-containing aggregates are subsequently dried and reduced to a relatively uniform particle size. The material thus obtained is packed into a column or formed into some other suitable reactor bed through which a glucose solution is passed to effect isomerization. Depending on the nature of the feed stock, further treatment of the emerging glucose-fructose solution (e.g., ion exchange resin "clean-up") may be carried out if desired.

The polyelectrolytes contemplated for use with this process are preferably water-soluble polymeric substances containing monomeric units which possess polar or ionizable groups. They are generally classified into three main categories —anionic, cationic and nonionic. Anionic polyelectrolytes usually contain carboxylic, sulfonic or phosphonic acid groups and examples of such materials include polyacrylic acid, polystyrenesulfonic acid, polyvinylphosphonic acid, carboxymethylcellulose, alginic acid and pectic acid. Most cationic polyelectrolytes involve the use of quaternary ammonium, sulfonium or phosphonium groups including the protonated forms of polyamines such as polyethylenimine and polyvinylpyridine. Additional examples of synthetic cationic polyelectrolytes may be found in a comprehensive review by M. F. Hoover, J. Macromol. Sci.—Chem. A4(6), pp. 1327–1417 (1970). Nonionic polyelectrolytes are exemplified by polyacrylamide and polyvinyl alcohol.

Obviously, polyelectrolytes having characteristics of more than one of the above categories may also be used in the process disclosed herein. For example, partial hydrolysis of polyacrylamide would produce a polyelectrolyte having both amide (non-ionic) and carboxylic acid (anionic) groups. Combinations of polyelectrolytes are also useful for this invention. Among the specific polyelectrolytes which are effective for use in accordance with this invention are Catfloc (Calgon Corp. of Pittsburg, Pa.), Delfloc 40 and Delfloc 763 (Hercules Inc. of Atlanta, Ga.), Dow XD-1923 (Dow Chemical Co. of Midland, Mich.), Natron 86 (National Starch & Chemical Corp. of Plainfield, N.J.), and Primafloc A-10 and Primafloc C-7 (Rohm & Haas of Philadelphia, Pa.).

The formation of the aggregate comprising the polyelectrolyte material and the enzyme-containing material is preferably effected by combining solutions or suspensions of the materials. This process is usually referred to as flocculation and the aggregate or floc that is formed is generally characterized by a loose, three-dimensional network. This is an important feature in that the enzyme-containing material immobilized in the floc is still accessible to substrate solutions contacted with the floc. It is important that agitation of the flocculation medium be gentle and that the amount of polyelectrolyte relative to the amount of enzyme containing material be carefully controlled. Sufficient polyelectrolyte is needed to effect satisfactory recovery of the enzyme-containing material; however, excessive amounts of polyelectrolyte are also to be avoided because the formed floc tends to redisperse in the presence of excess flocculant. The amount of polyelectrolyte required will also be influenced by the presence of other materials in the flocculating medium. For example, the flocculation of washed glucose isomerase-containing microbial cells requires slightly less polyelectrolyte than cells which are flocculated directly in the fermentation broth. The particular microorganism involved will also determine the type and amount of polyelectrolyte needed. For glucose isomerase-producing microorganisms, the cationic polyelectrolytes are generally most effective and the amount of polyelectrolyte required relative to the wet weight of the enzyme-containing material is preferably in the range of 0.5 to 50 percent by weight. The temperature of the flocculating medium is maintained between about 10° and 40° C. and the pH is maintained at 5.0 to 9.5. The polyelectrolyte is preferably added in the form of a 1 to 2% aqueous solution and flocculation of the enzyme-containing material usually begins immediately, flocculation being complete within a few minutes. When satisfactory flocculation has been achieved, the formed aggregates have a feathery or flaky appearance and quickly settle out of the suspending liquid as soon as agitation is stopped. The harvested aggregates are also characterized by their ability to dewater readily upon filtration or centrifugation to give a reasonably dry material that is not slimy to the touch.

Optimum conditions for effecting flocculation are readily determined by experimentation. Table 1 shows results of a typical flocculant evaluation in which arbitrary ratings are assigned based on visual observations. Evaluated are the appearance and formation of the floc, the rapidity with which sedimentation or settling of the floc occurs, the degree of clarification of the liquid medium in which the flocculation is carried out and the filtering properties of the formed floc. Table 2 lists a similar evaluation for two different flocculating agents used together in effecting formation of the floc.

TABLE 1

Flocculation of 200 ml. of a 4.8% Suspension of *Arthrobacter* NRRL B-3728 Cells at 25° C. With Dilute Catfloc Solution

| ml. 10-Fold Diluted Catfloc Soln. | Flocculation | Sedimentation | Clarification | Filtration |
| --- | --- | --- | --- | --- |
| 0.5 | fair | fair | fair | poor |
| 1.0 | fair | fair | fair | poor |
| 5.0 | fair | fair | fair | poor |
| 10.0 | fair | fair | fair | poor |
| 20.0 | very good | very good | good | good |
| 40.0 | very good | very good | very good | good |
| 60.0 | very good | very good | very good | good |
| 80.0 | fair | fair | poor | poor |
| 100.0 | poor | poor | poor | poor |

TABLE 2

Flocculation of 200 ml. of a 5% Suspension of *Streptomyces phaeochromogenes* NRRL B-3559 Cells at 25° C. With Dilute Primafloc C-7 Plus Dilute Primafloc A-10

| ml. of 1% Flocculant | | Flocculation | Sedimentation | Clarification | Filtration |
| --- | --- | --- | --- | --- | --- |
| C-7* | A-10 | | | | |
| 0.5 | 0.5 | fair | fair | fair | poor |
| 1.0 | 1.0 | good | good | fair | fair |
| 5.0 | 5.0 | very good | very good | good | good |
| 10.0 | 10.0 | very good | very good | very good | good |
| 15.0 | 15.0 | excellent | excellent | excellent | excellent |
| 20.0 | 20.0 | excellent | excellent | excellent | excellent |
| 40.0 | 40.0 | excellent | excellent | excellent | excellent |
| 80.0 | 80.0 | excellent | excellent | excellent | excellent |
| 160.0 | 160.0 | excellent | excellent | excellent | excellent |

*Added before the Primafloc A-10.

The source of glucose isomerase-containing material used in the practice of this invention is not critical. A number of microorganisms have been disclosed in the prior art as being capable of elaborating glucose isomerase including species of the genera Arthrobacter, Lactobacillus, Pasteurella, Aerobacter, Streptomyces and Leuconostoc. Species of Arthrobacter and Streptomyces are particularly preferred as sources of isomerase. The microorganism selected is cultured in an appropriate nutrient medium to induce formation of isomerase. At the conclusion of the fermentation period, the isomerase-containing cell material is recovered and immobilized.

In one preferred embodiment of this invention, the isomerase is immobilized by flocculation of the isomerase-containing cells directly in the fermentation broth. This eliminates a separate cell-harvesting operation and also converts the cells into a more easily recoverable form. If harvesting of the microbial cells prior to flocculation is desired, the cells are collected and washed in the usual manner before resuspending in an aqueous medium (wet cell concentration of 2 to 10 percent is preferred) and flocculating. Additional processing of the cells such as lysing, sonic treatment, mechanical abrasion, etc. may also be carried out prior to flocculation. Such treatment, preferably, should have no detrimental effect on isomerase activity contained in the cell debris.

Following treatment with the polyelectrolyte to form the aggregate containing the cell material, the aggregate is removed from the flocculating medium by conventional procedures such as centrifugation or filtration. The collected aggregate is then subjected to an optional extrusion step to convert the material into a shape and size which permit more uniform drying and/or more uniform packing into a bed for glucose isomerization. Excess water in the harvested floc at this point should be avoided. A moisture content of about 60–70 percent by weight based on the weight of the dried material (described below) is satisfactory. In carrying out the extrusion step high pressures are to be avoided because undue compaction of the floc tends to destroy the porous nature of the floc. Extrusion of a typical harvested floc has been obtained using a Model EXDCS-100 extruder equipped with a 30-mesh screen as supplied by Elanco Extruder Products Company of Indianapolis, Ind.

The extruded floc is dried at ambient temperatures or, more preferably, at elevated temerature, not to exceed approximately 60° C. The preferred drying temperature is 50° to 60° C. The actual drying device used is not particularly critical although forced draft ovens are preferred. Drying is continued until the extrudate is dry or brittle enough to permit milling of the material as well as to permit storage of the dried material for extended periods of time. A residual moisture level of 5 to 15 percent for the dried extrudate is generally satisfactory for both milling and storage. It should be pointed out that drying of the extruded floc is not essential if the extrudate is to be used immediately in an isomerase reactor bed. Under normal operating conditions, however, stockpiling of the immobilized enzyme is desirable. Such stockpiling is most conveniently effected by converting the isomerase-containing material to the dried form so that it may be stored for an extended period of time prior to use.

Milling of the dried, extruded floc is another optional feature of the present invention. Reduction of the particle size by milling or similar mechanical treatment followed by a sieving operation allows the selection of a particular particle size for use in a glucose isomerization process. The particle size selected will be somewhat dependent on substrate flow rates and the degree of glucose isomerization desired. Broadly preferred particle sizes for use in the process disclosed herein are in the 10 to 30 mesh range as defined by the U.S. Bureau of Standards and more particularly in the 16 to 20 mesh range.

The isomerase-containing material produced by the polyelectrolyte treatment is very effective for converting glucose to fructose. This conversion is most conveniently carried out continuously by passing a glucose syrup through a suitable bed of the material although a batch-type process may be employed if desired. For a continuous process a suspension of the isomerase-containing material is first prepared by adding the material to a solution containing a magnesium salt and a suitable buffer which will maintain the solution at a pH of about 8 to 9. The magnesium salt serves to enhance the isomerase activity and the buffering agent tends to remove any acidic materials which could cause denaturation of the enzyme. It has been found that a solution which is 0.05 molar with respect to sodium bicarbonate and 0.01 molar with respect to magnesium chloride is satisfactory for preparing a suspension of the isomerase-containing material. When using the dried material for preparing this suspension, the slurry should be permitted to stand for 30 to 60 minutes to allow the individual particles to swell. The suspension is then carefully poured into a suitable column containing additional quantities of the sodium bicarbonate-magnesium chloride solution so that entrapment of air bubbles is avoided. Continued pretreatment of the reactor bed with the sodium bicarbonate-magnesium chloride solution for a period of time is desirable in that maximum isomerase activity is reached more quickly than in the case where a glucose solution is passed through the reactor bed immediately after preparation of the bed. The length of time required for this pretreatment will depend on the size of the reactor bed and flow rates of the solution through the bed. Generally speaking, a volume of solution equivalent to at least twice the volume occupied by the reactor bed should be passed through the bed to achieve the desired effect. It is believed that the effectiveness of this pretreatment is due to the removal of calcium ions and other materials which tend to inactivate the isomerase.

The dimensions of the reactor bed are determined by the substrate flow rate and degree of glucose isomerization desired. The bed depth should be sufficient to minimize channeling. For columns of circular cross section it is preferred that the depth to diameter ratio be at least one. The glucose syrup is most conveniently passed through the reactor bed by allowing the syrup to flow downwardly through the bed by gravity; however, upward flow or horizontal flow may also be used by employing appropriate apparatus and equipment according to known technology. The apparatus containing the reactor bed should be provided with heating means so that the isomerase-containing material can be maintained at temperatures above ambient and preferably between 50° and 75° C.

The concentration of the glucose syrup used as feed stock in this process is not critical. It is preferred that a purified dextrose solution of 30 to 60 percent by weight or a high DE (i.e., DE greater than 94) starch conversion syrup having a solids content of 30 to 50 percent by weight be used as the feed solution. The degree of glucose isomerization obtainable by this process may range as high as 55 percent.

Reference will now be made to the drawings to describe more clearly how the process of this invention is carried out.

Figure 1:
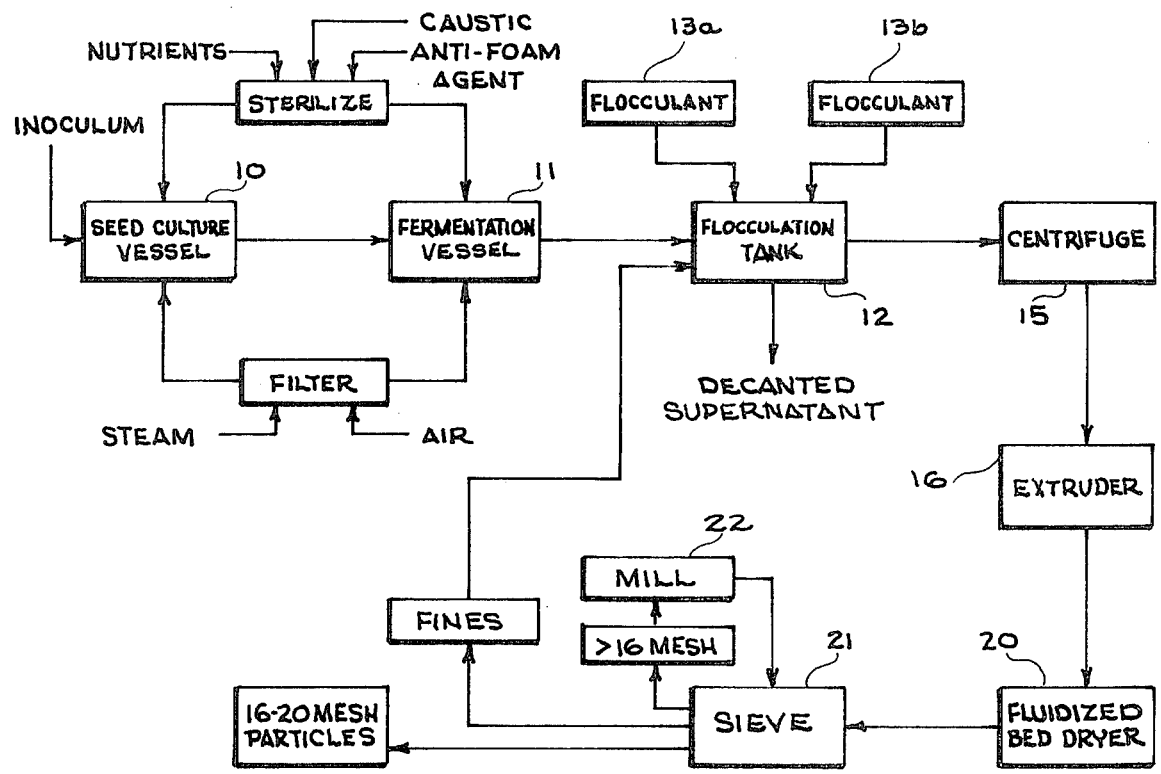
FIG. 1 is a flow diagram showing how dried, flocculated microbial cell material containing glucose isomerase may be prepared for use in the process of this invention.

As depicted in FIG. 1, inoculum for large fermentation vessel 11 is prepared in appropriately-sized seed culture vessel 10. Both vessels are provided with means for introducing sterilized nutrients, caustic, air and antifoam agent. They may be further provided with suitable pH monitoring devices and foam detectors by means of which automatic addition of caustic or antifoam agent, respectively, may be effected. Fermentation is allowed to proceed in vessel 11 until the desired cell yield is obtained. The culture broth is then pumped into flocculation tank 12 where it is treated with one or more solutions of flocculating agents that have been previously prepared in the flocculant make-up tanks 13a and 13b. The resulting flocculated cells are allowed to settle to the bottom of flocculation tank 12 and a portion of the clarified supernatant is decanted from the tank. Recovery of the flocculated cells is effected in centrifuge 15 and the moist floc is extruded by means of extruder 16. Drying in fluidized bed dryer 20 is followed by screening and sizing of the dried floc particles in sieve 21. Material in the 16–20 mesh range is recovered and stored for subsequent use in a glucose isomerization process while the larger particles are milled in mill 22 and returned to sieve 21, the fines being returned to flocculation tank 12 for recycling.

Figure 2:
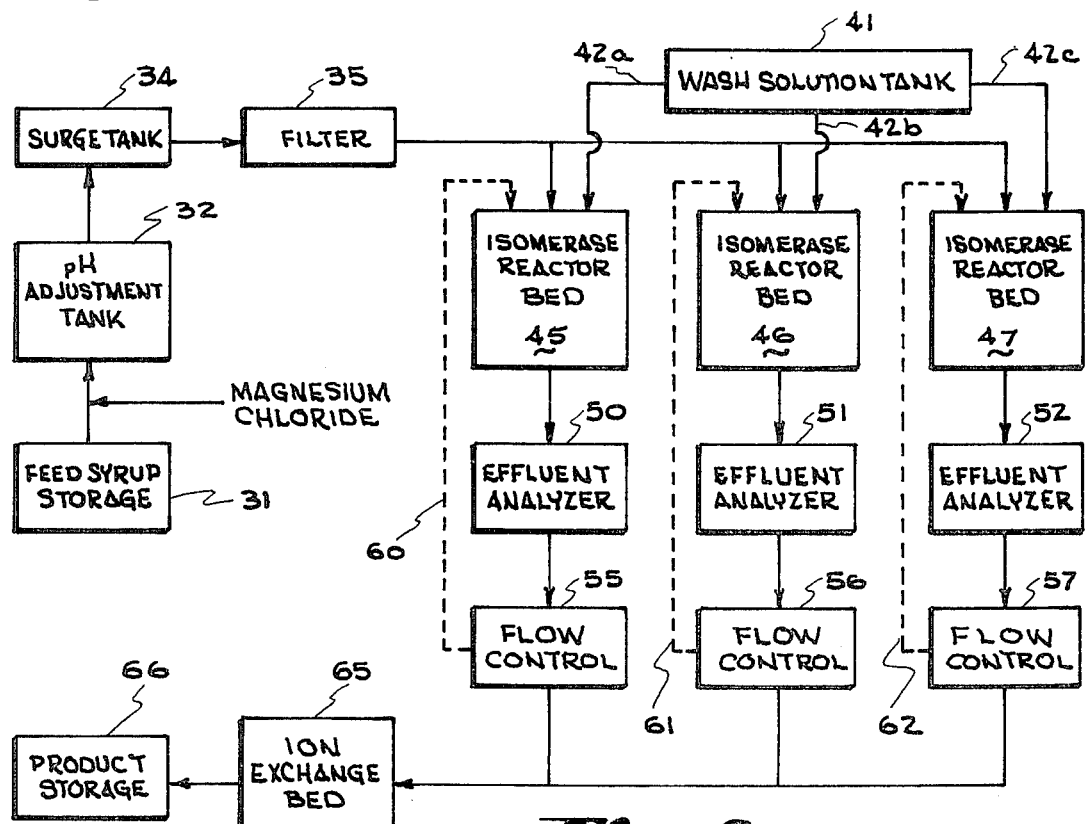
FIG. 2 is a flow diagram showing how glucose isomerization is carried out by utilizing immobilized, glucose isomerase-containing microbial cell material.

Isomerization of glucose is carried out as shown in FIG. 2. A glucose-containing feed syrup is pumped from storage tank 31 into tank 32 where pH of the syrup is adjusted to about 8.0 by the addition of dilute sodium hydroxide. Sufficient magnesium chloride is added to the syrup prior to entry into tank 32 to give a concentration of about 0.004 molar. After passing through surge tank 34 and filter 35 to remove any undissolved solids, the feed syrup is directed to isomerase reactor beds 45, 46 and 47 which contain flocculated microbial cell material. Wash solution tank 41 and lines 42a, b and c provide means for introducing a dilute sodium bicarbonate-magnesium chloride solution into each isomerase reactor bed during the start-up procedure. The reactor beds are provided with suitable means for heating (not shown) so that glucose isomerization can be carried out at a constant temperature of about 60° C. Substrate flow rates through reactor beds 45, 46 and 47 are controlled by flow controls 55, 56 and 57, respectively, to give syrups containing the desired proportion of fructose. Composition of the effluent syrups is constantly monitored by glucose-fructose analyzers 50, 51 and 52 which measure the optical rotation and refractive index of the effluent streams. The effluent streams entering flow controls 55, 56 and 57 may be recycled to reactor beds 45, 46 and 47 via lines 60, 61 and 62, respectively, in the event that the degree of glucose isomerization is too low. Otherwise, the effluent streams are routed to ion exchange bed 65 for final refinement of the product syrup. The pH of the product syrup is adjusted to approximately 5.0 prior to accumulating the syrup in storage tank 66 to insure maximum stability of the fructose.

The following examples will further illustrate the process of this invention:

EXAMPLE 1

The cultivation of Arthrobacter nov. sp. NRRL B-3728 was carried out as described in U.S. Pat. No. 3,645,848 to give 400 gallons of culture broth having a pH of 5.7. This broth was gently agitated and to it were added 53.3 gallons of a 1.5% solution of Primafloc C-7 (previously adjusted to pH 5.0) followed immediately with 53.3 gallons of a 1.5% solution of Primafloc A-10. Addition of the flocculating agents was effected over a period of about 15 minutes and flocculation of the cells was essentially complete within 20 minutes. Centrifugation yielded 125 pounds of wet, flocculated cells having a moisture content of approximately 80%. This wet floc was then extruded through a 30-mesh screen using a Model EXDCS-100 extruder supplied by Elanco Extruder Products Company of Indianapolis, Ind. The extruded floc was subsequently dried at 55°–60° C. by means of a fluidized bed dryer (Type TF-30 Glatt Dryer) available from Artisan Industries of Waltham, Mass. 02154, giving 30 pounds of dried material having a moisture content of slightly less than 10%. The dried, flocculated cells retained their isomerase activity which activity was undiminished even after storage for 7 months at room temperature.

The dried, flocculated cell material was milled and sieved to give particles in the 16–20 mesh range (U.S. Bureau of Standards). A 3-gram portion of the 16–20 mesh material was suspended in an aqueous solution that was 0.05 molar with respect to sodium bicarbonate and 0.01 molar with respect to magnesium chloride. After the particles had swelled to the maximum extent, they were packed into a 1-inch diameter glass column and the floc particles were washed by passing additional quantities of the sodium bicarbonate-magnesium chloride solution through the packed bed equivalent to approximately three times the volume occupied by the packed bed. The packed column was heated to 60° C. and a 2.0 M dextrose solution containing 0.004 M magnesium chloride (previously adjusted to pH 8.5 with sodium hydroxide) was passed through the column at a constant flow rate of 950 milliliters per day. The syrup emerging from the column was analyzed daily for fructose content. The degree of glucose to fructose conversion obtained initially was 35.9% and after 28 days it had declined to 32.8%.

EXAMPLE 2

The cultivation of *Streptomyces olivochromogenes* was carried out as described in U.S. Pat. No. 3,622,463. The mycelia were harvested by centrifugation and washed. A 200 gram portion of the wet mycelia was resuspended in 4 liters of water and treated sequentially with 300 milliliters of a 1.5% solution of Primafloc C-7 (previously adjusted to pH 8.0) and 100 milliliters of a 1.5% solution of Primafloc A-10 (previously adjusted to pH 8.0). Gentle agitation was continued for a few minutes before recovering the flocculated mycelia by vacuum filtration. The wet, flocculated mycelia were dried in an oven for 18 hours at 56° C. to yield 40 grams of dry material. This dry floc was crushed in a Micro-Wiley mill and was sieved to obtain particles of 16–20 mesh size (U.S. Bureau of Standards). A 4-gram portion of the dry, 16–20 mesh material was suspended in an aqueous solution that was 0.05 molar with respect to sodium bicarbonate and 0.01 molar with respect to magnesium chloride. After the particles had swelled to the maximum extent, they were packed into a 1-inch diameter glass column and the floc particles were washed by passing 4 liters of additional sodium bicarbonate-magnesium chloride solution through the packed bed over a 2-hour period. The packed column was heated to 60° C. and a 2.0 M dextrose solution containing 0.004 M magnesium chloride was passed through the column at a constant flow rate of 1150 milliliters per day. The pH of the feed syrup was adjusted periodically by adding sufficient 1.0 N sodium hydroxide to give an effluent syrup with pH 8.0–8.2. The initial degree of glucose to fructose conversion was approximately 42% and after 1 month of continuous operation, conversion had declined to about 39%.

The advantages of this invention are readily apparent from the foregoing description. It will be appreciated that any number of variations in the basic process described herein may be made. Those modifications and equivalents which fall within the spirit of the invention and scope of the appended claims are to be considered part of the invention.

What is claimed is:

1. A continuous process for isomerizing glucose to fructose in the presence of glucose isomerase-containing microbial cells wherein said cells are used in the form of an aggregate resulting from prior treatment of said cells with 0.5 to 50 percent by weight based on the wet weight of said cells of a polyelectrolyte flocculating agent followed by drying and sieving of the aggregate to produce dried aggregate particles that are approximately 10 to 30 mesh in size, said continuous process comprising passing a glucose solution through a bed of said aggregate at a temperature of 50° to 90° C. and a pH of 6 to 10 to effect isomerization of a portion of the glucose and recovering an effluent syrup containing glucose and fructose.

2. A process according to claim 1 in which said aggregate is dried to a moisture level of less than 15 percent prior to use in the glucose isomerization process.

3. A process according to claim 2 in which the cells are derived from a microorganism belonging to the genus Arthrobacter.

4. A process according to claim 2 in which the cells are derived from a microorganism belonging to the genus Streptomyces.

5. A continuous process for converting glucose to fructose in the presence of glucose isomerase-containing microbial cells wherein said cells are used in the form of an aggregate resulting from prior flocculation of said cells with 0.5 to 50 percent by weight based on the wet weight of said cells of a polyelectrolyte flocculating agent selected from the group consisting of anionic and cationic polyelectrolytes followed by
  a. harvesting the flocculated cells,
  b. extruding the harvested flocculated cells, and
  c. drying the extruded flocculated cells to a moisture level of less than 15 percent,
said continuous process comprising passing a glucose solution through a bed of said aggregate at a temperature of 50° to 90° C. and a pH of 6 to 10 to effect conversion of a portion of the glucose to fructose and recovering an effluent syrup containing glucose and fructose.

6. A process according to claim 5 in which the aggregate contains both an anionic and a cationic polyelectrolyte.

7. A process according to claim 6 in which the aggregate is used in the form of particles that are approximately 10 to 30 mesh in size when dry.

8. A process according to claim 7 in which the microbial cells are derived from a microorganism belonging to the genus Arthrobacter.

9. A process according to claim 7 in which the microbial cells are derived from a microorganism belonging to the genus Streptomyces.

* * * * *